US008529531B2

(12) United States Patent
Park et al.

(10) Patent No.: US 8,529,531 B2
(45) Date of Patent: Sep. 10, 2013

(54) MEDICAL TISSUE EXTRACTION INSTRUMENT

(75) Inventors: Young Sam Park, Jeonju-si (KR); Cheol Seung Kim, Jeonju-si (KR)

(73) Assignee: The Presbyterian Medical Center Juridical Person (KR)

( * ) Notice: Subject to any disclaimer, the term of this patent is extended or adjusted under 35 U.S.C. 154(b) by 191 days.

(21) Appl. No.: 13/027,746

(22) Filed: Feb. 15, 2011

(65) Prior Publication Data
US 2011/0202015 A1 Aug. 18, 2011

(30) Foreign Application Priority Data

Feb. 18, 2010 (KR) .................. 10-2010-0014722

(51) Int. Cl.
*A61M 1/00* (2006.01)
(52) U.S. Cl.
USPC .......... 604/319; 604/19; 604/317; 604/540
(58) Field of Classification Search
USPC .................... 604/319, 19, 317, 540
See application file for complete search history.

(56) References Cited

U.S. PATENT DOCUMENTS

| | | | | | |
|---|---|---|---|---|---|
| 3,929,133 | A | * | 12/1975 | Ragab | 604/119 |
| 4,493,698 | A | * | 1/1985 | Wang et al. | 604/541 |
| 4,650,460 | A | * | 3/1987 | Roizenblatt | 604/22 |
| 4,770,654 | A | * | 9/1988 | Rogers et al. | 604/22 |
| 4,773,897 | A | * | 9/1988 | Scheller et al. | 604/34 |
| 4,790,816 | A | * | 12/1988 | Sundblom et al. | 604/31 |
| 4,830,047 | A | * | 5/1989 | Hodge | 137/505.13 |
| 4,857,063 | A | * | 8/1989 | Glenn | 604/317 |
| 5,024,653 | A | * | 6/1991 | Kohnke | 604/35 |
| 5,098,416 | A | * | 3/1992 | Imonti | 604/319 |
| 5,403,276 | A | * | 4/1995 | Schechter et al. | 604/22 |
| 5,522,808 | A | * | 6/1996 | Skalla | 604/319 |
| 5,575,293 | A | * | 11/1996 | Miller et al. | 600/565 |
| 5,643,304 | A | * | 7/1997 | Schechter et al. | 606/171 |
| 6,017,354 | A | * | 1/2000 | Culp et al. | 606/170 |
| 6,179,829 | B1 | * | 1/2001 | Bisch et al. | 606/1 |
| 6,322,549 | B1 | * | 11/2001 | Eggers et al. | 604/500 |
| 6,428,508 | B1 | * | 8/2002 | Ross | 604/118 |
| 6,629,986 | B1 | * | 10/2003 | Ross et al. | 606/171 |
| 7,012,203 | B2 | * | 3/2006 | Hanson et al. | 200/86.5 |
| 7,422,432 | B2 | * | 9/2008 | Warner | 433/101 |
| 7,470,277 | B2 | * | 12/2008 | Finlay et al. | 606/166 |
| 7,659,833 | B2 | * | 2/2010 | Warner et al. | 340/12.5 |
| 8,048,094 | B2 | * | 11/2011 | Finlay et al. | 606/166 |
| 8,409,155 | B2 | * | 4/2013 | Wong et al. | 604/290 |
| 2003/0047434 | A1 | * | 3/2003 | Hanson et al. | 200/86.5 |
| 2003/0073980 | A1 | * | 4/2003 | Finlay et al. | 606/1 |
| 2004/0049217 | A1 | * | 3/2004 | Ross et al. | 606/171 |
| 2006/0047185 | A1 | * | 3/2006 | Shener et al. | 600/156 |
| 2008/0249553 | A1 | * | 10/2008 | Gruber et al. | 606/171 |

* cited by examiner

*Primary Examiner* — Tatyana Zalukaeva
*Assistant Examiner* — Ginger T Chapman
(74) *Attorney, Agent, or Firm* — Cantor Colburn LLP

(57) ABSTRACT

Disclosed is a medical tissue extraction instrument, which can allow an inspector to accurately locate a fine needle at a desired tissue extraction position without any need for assistance while assuring stable tissue extraction. The medical tissue extraction instrument includes a tissue extraction controller to control the pressure of a suction tube connected to a fine needle during extraction of tissue. The tissue extraction controller includes a suction pressure generator taking the form of a footboard and adapted to control a suction operation of the suction tube by being pushed downward.

2 Claims, 3 Drawing Sheets

MEDICAL TISSUE EXTRACTION INSTRUMENT

BACKGROUND OF THE INVENTION

1. Field of the Invention

The present invention relates to a medical tissue extraction instrument, and more particularly to a tissue extraction instrument, which can accurately locate a fine needle at a desired tissue extraction position and perform stable control of a suction operation thereof when attempting to extract tissue from a patient's body.

2. Description of the Related Art

Generally, collection or extraction of biological tissue is required to perform diagnosis, biochemical analysis, genetic analysis, and the like.

FIG. 1 is a view illustrating fine needle aspiration cytology inspection performed under ultrasonic guidance using a conventional tissue extraction instrument. During the needle aspiration cytology inspection, an operator attempts to insert a fine needle 11 of the tissue extraction instrument into a tissue extraction region of the patient's body using one hand while gripping an ultrasonic transducer 50 in the other hand.

Then, if an assistant pulls a piston of a syringe 31 of the tissue extraction instrument, tissue is extracted through a suction tube 21 connecting the fine needle 11 to the syringe 31.

When using the above described conventional tissue extraction instrument, however, the operator has difficulty extracting tissue without an assistant.

In addition, since the assistant is allowed to pull the syringe, but the syringe functions to control a suction operation during extraction of tissue, there is a risk of unintentional position change or separation of the fine needle. Moreover, it is difficult for the operator to directly control suction pressure and suction period based on different tissue extraction conditions, which results in deterioration in the stability of extraction of tissue.

SUMMARY OF THE INVENTION

Therefore, the present invention has been made in view of the above problems, and it is one object of the present invention to provide a medical tissue extraction instrument, which allows an inspector to accurately aim a fine needle at a tissue extraction region of a patient's body without the help of an assistant and to perform stable extraction of tissue.

It is another object of the present invention to provide a medical tissue extraction instrument, which includes a suction pressure generator enabling easy control of the pressure of a suction tube.

It is another object of the present invention to provide a medical tissue extraction instrument, which further includes a tissue collector to easily collect extracted tissue.

It is another object of the present invention to provide a medical tissue extraction instrument, which includes a suction adjustor to keep a suction tube at a constant pressure.

It is another object of the present invention to provide a medical tissue extraction instrument, which includes a suction adjustor to easily set suction pressure and suction period.

It is a further object of the present invention to provide a medical tissue extraction instrument, which includes two or more pressure boards to selectively perform a continuous suction operation and a discontinuous suction operation, which enables ease in operation.

In accordance with the present invention, the above and other objects can be accomplished by the provision of a medical tissue extraction instrument including a tissue extraction controller to control the pressure of at least one suction tube connected to a fine needle during extraction of tissue.

The tissue extraction controller may include a suction pressure generator taking the form of a footboard and adapted to control a suction operation of the suction tube by being pushed downward.

The tissue extraction controller may include a suction adjustor to set the pressure applied to the suction tube.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, practical application of a medical tissue extraction instrument according to the present invention will be described in detail.

Figure 1:
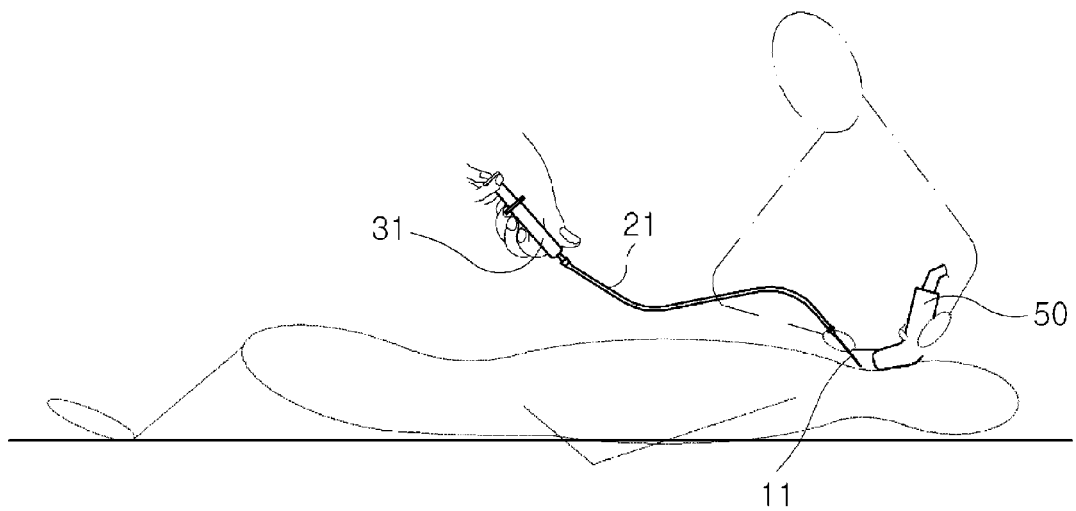
FIG. 1 is a view illustrating an operation using a conventional medical tissue extraction instrument.
Figure 2:
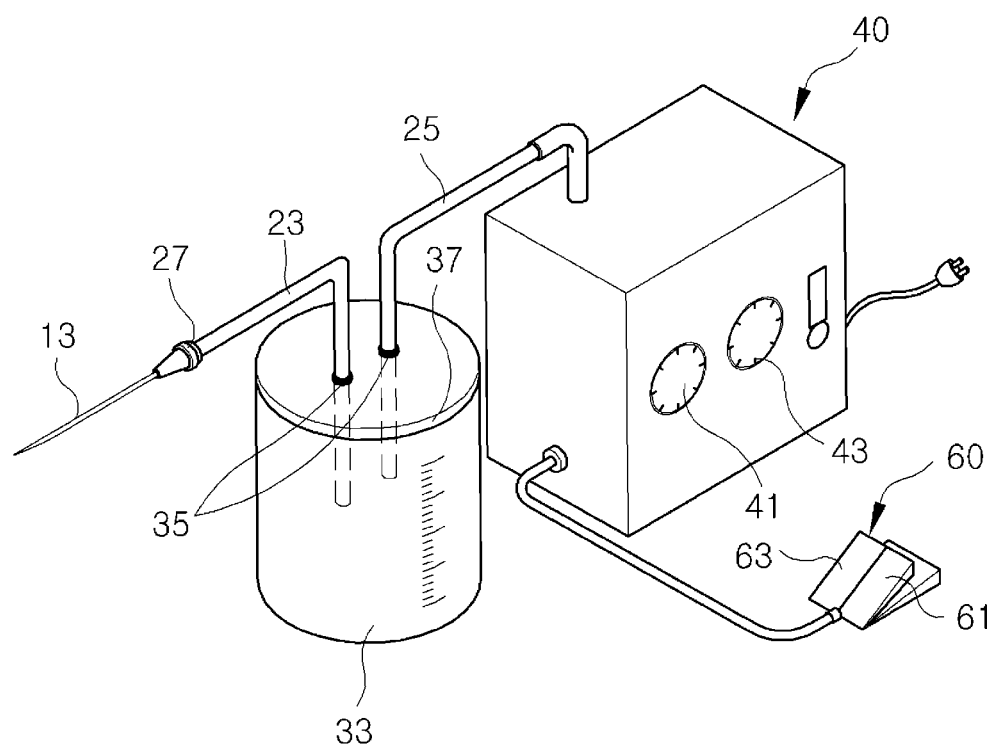
FIG. 2 is a view illustrating a configuration of a medical tissue extraction instrument according to the present invention.

FIG. 2 is a view illustrating a configuration of the medical tissue extraction instrument according to the present invention. As illustrated, the medical tissue extraction instrument includes a fine needle 13, suction tubes 23 and 25, a tissue collector 33, and a tissue extraction controller 40.

The fine needle 13 takes the form of a metal tube to be inserted into a tissue extraction region of a patient. One end of the fine needle 13 is inserted into the body of the patient and the other end of the fine needle 13 is connected to the first suction tube 23.

The first suction tube 23 connected to the fine needle 13 serves as a movement tube of biological tissue extracted via the fine needle 13. Changing the air pressure of the suction tube 23 may control whether or not the fine needle 13 begins to extract tissue.

The extracted biological tissue is moved into the tissue collector 33 through the first suction tube 23.

The tissue collector 33 provides a space for receiving the extracted biological tissue. Preferably, the tissue collector 33 is externally provided with scales or other graduations to aid in easy recognition of the quantity of the extracted biological tissue.

In an embodiment of the present invention, the tissue collector 33 is provided at the top thereof with connection holes for connection of the first suction tube 23 and the second suction tube 25. Preferably, the first and second suction tubes 23 and 25 are tightly inserted into the connection holes with rubber packing members 35 interposed therebetween, so as to prevent leakage of the extracted biological tissue or the interior air of the suction tubes 23 and 25.

In addition, the tissue collector 33 is further preferably provided at the top thereof with an opening/closing lid 37 to help the operator to easily inspect the tissue received in the tissue collector 33.

The second suction tube 25 is connected at one end thereof to the top of the tissue collector 33 and at the other end thereof to the tissue extraction controller 40.

The tissue extraction controller 40 serves to control the pressure of the second suction tube 25. Preferably, according to the present invention, the tissue extraction controller 40 is externally provided with a suction adjustor to adjust pressure applied to the interior of the suction tube 25.

The suction adjustor according to the present invention includes a pressure adjustor 41 and a suction period adjustor 43.

The pressure adjustor 41 serves to adjust the pressure inside the suction tubes 23 and 25.

The suction period adjustor 43 serves to adjust a suction period of tissue extracted into the first suction tube 23.

When the suction period adjustor 43 is used, furthermore, it is possible to set a generation period of pressure applied to the interior of the suction tubes 23 and 25, which enables automatic extraction of tissue at regular intervals.

The tissue extraction controller 40 according to the present invention includes a suction pressure generator 60 in the form of a footboard.

The suction pressure generator 60 includes upper pressure boards 61 and 63 by which the operator generates suction pressure. That is, the suction operation of the suction tubes 23 and 25 is controlled by controlling force applied to the pressure boards 61 and 63.

The pressure boards 61 and 63 may include two or more pressure boards. In the embodiment of the present invention, the pressure boards 61 and 63 may be a continuous suction pressure board 61 and a discontinuous suction pressure board 63.

The continuous suction pressure board 61 serves to allow the suction tubes 23 and 25 to perform successive suction operations.

The discontinuous suction pressure board 63 serves to allow the suction tubes 23 and 25 to perform intermittent suction operations.

Figure 3:
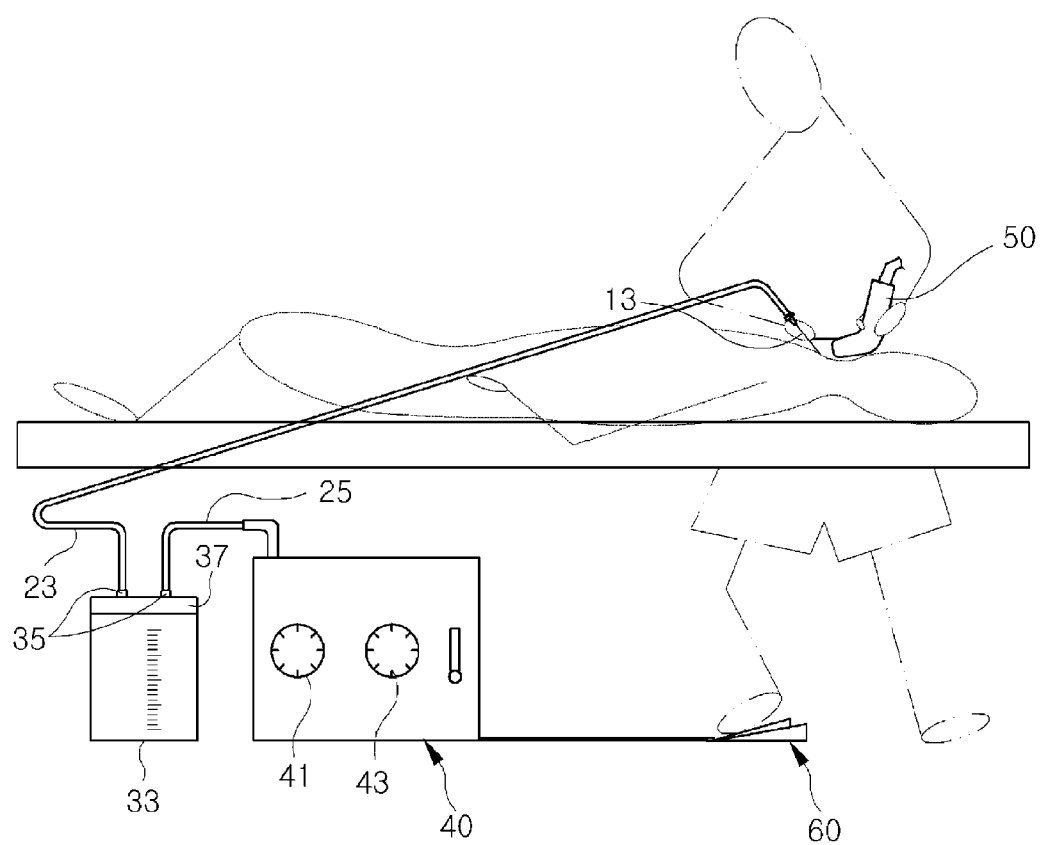
FIG. 3 is a view illustrating an operation using the medical tissue extraction instrument according to the present invention.

FIG. 3 is a view illustrating an operation using the medical tissue extraction instrument according to the present invention. During operation, as illustrated, the operator or the inspector attempts to insert the fine needle 13 into a tissue extraction region of the patient's body using one hand while gripping an ultrasonic transducer 50 in the other hand.

In this case, the interior pressures of the suction tubes 23 and 25 are adjusted based on the suction pressure and the suction period set by the pressure adjustor 41 and the suction period adjustor 43 of the tissue extraction controller 40.

Through the suction operation of the suction tubes 23 and 25, the biological tissue extracted via the fine needle 13 is moved into the tissue collector 33 through the first suction tube 23.

In this case, the operator or the inspector may control the suction operation by selectively pushing any one of the continuous suction pressure board 61 and the discontinuous suction pressure board 63 of the suction pressure generator 60.

For example, if the continuous suction pressure board 61 is pushed, the suction operation may be performed successively and periodically based on the suction period set by the suction period adjustor 43. On the other hand, the operator may control the suction operation as occasion demands by selectively pushing the discontinuous suction pressure board 63.

As is apparent from the above description, the present invention provides a medical tissue extraction instrument according to the present invention, which allows an operator (or an inspector) to control a suction operation thereof without any need for assistance. Accordingly, the operator is capable of accurately aiming a fine needle at a tissue extraction region of the patient's body and stably performing tissue extraction.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. A medical tissue extraction instrument comprising a tissue extraction controller to control pressure of at least one suction tube connected to a fine needle during extraction of tissue, wherein
    the tissue extraction controller includes a suction adjustor to set pressure applied to a suction tube, the suction adjustor including a pressure adjustor to adjust the pressure applied to the suction tube and a suction period adjustor to adjust a suction period at which the tissue is extracted into the suction tube, thereby enabling automatic extraction of the tissue into the suction tube at regular intervals, and wherein
    the tissue extraction controller further includes a suction pressure generator taking a form of a footboard and adapted to control a suction operation of the suction tube when being pushed downward, the suction pressure generator including two or more pressure boards, each including a continuous suction pressure board to perform successive suction operations of the suction tube according to the suction period and a discontinuous suction pressure board to perform intermittent suction operations of the suction tube.

2. The medical tissue extraction instrument according to claim 1, further comprising a tissue collector to receive the tissue extracted via the fine needle,
    wherein the at least one suction tube includes a first suction tube connected at one end thereof to the fine needle and a second suction tube connected at one end thereof to the tissue extraction controller, and
    wherein the other end of the first suction tube and the other end of the second suction tube are connected to the tissue collector with packing members interposed therebetween.

* * * * *